United States Patent
Coburn et al.

(10) Patent No.: US 11,110,203 B2
(45) Date of Patent: Sep. 7, 2021

(54) DECELLULARIZATION OF PLANT CELL CULTURE MATERIALS FOR TISSUE ENGINEERING AND DRUG DELIVERY

(71) Applicant: Worcester Polytechnic Institute, Worcester, MA (US)

(72) Inventors: Jeannine Coburn, Worcester, MA (US); Glenn Gaudette, Worcester, MA (US); Nhi Phan, Worcester, MA (US)

(73) Assignee: Worcester Polytechnic Institute, Worcester, MA (US)

(*) Notice: Subject to any disclaimer, the term of this patent is extended or adjusted under 35 U.S.C. 154(b) by 57 days.

(21) Appl. No.: 16/548,510

(22) Filed: Aug. 22, 2019

(65) Prior Publication Data

US 2020/0061245 A1     Feb. 27, 2020

Related U.S. Application Data

(60) Provisional application No. 62/721,371, filed on Aug. 22, 2018.

(51) Int. Cl.
*C12N 5/00*   (2006.01)
*A61L 27/36*  (2006.01)

(52) U.S. Cl.
CPC ........ *A61L 27/3695* (2013.01); *C12N 5/0025* (2013.01); *C12N 2509/00* (2013.01); *C12N 2533/54* (2013.01); *C12Y 301/01* (2013.01); *C12Y 302/01022* (2013.01); *C12Y 304/21004* (2013.01); *C12Y 304/24007* (2013.01); *C12Y 304/24027* (2013.01)

(58) Field of Classification Search
None
See application file for complete search history.

(56) References Cited

U.S. PATENT DOCUMENTS

| 2010/0008967 | A1  | 1/2010 | Grande et al. |
| 2010/0137203 | A1* | 6/2010 | Min ................ A61P 19/08 514/21.5 |
| 2015/0017140 | A1  | 1/2015 | Bhatia et al. |

FOREIGN PATENT DOCUMENTS

| WO | WO-2017136950 A1 * | 8/2017 | ............ A61P 43/00 |
| WO | 2017160862 A1 | 9/2017 | |

OTHER PUBLICATIONS

Crapo et al, 2011, Biomaterials, 32:3233-3243.*
Gower et al, 2013, Advances in Wound Care, 2:100-106.*
Elder et al, 2010, Neurosurgery, 66:722-727.*
PCT International Search Report and Written Opinion issued in International Application No. PCT/US2019/047742 dated Dec. 13, 2019.

* cited by examiner

*Primary Examiner* — Jason Deveau Rosen
(74) *Attorney, Agent, or Firm* — Greenberg Traurig, LLP; Roman Fayerberg

(57) ABSTRACT

Provided herein are enzymatically decellularized cells, and methods of producing said cells, that can be used in a scaffold. The scaffolds featured herein are biocompatible and can comprise decellularized cells that have been modified to express a bioactive agent or molecule.

12 Claims, 17 Drawing Sheets

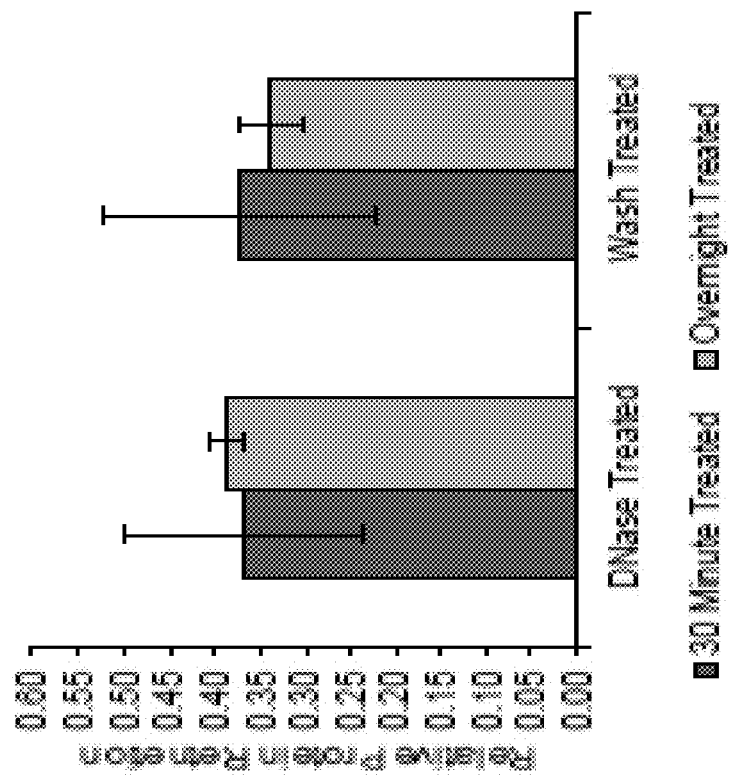
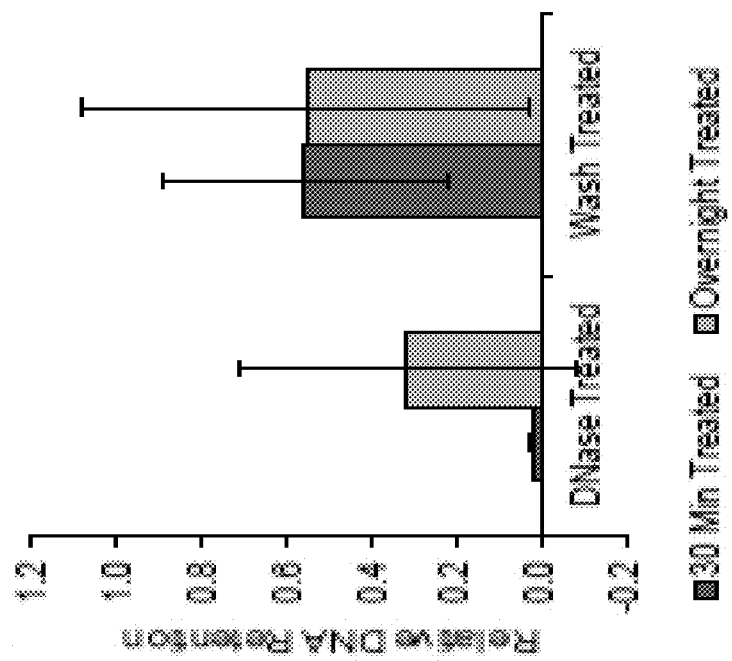
Fig. 7A
Fig. 7B

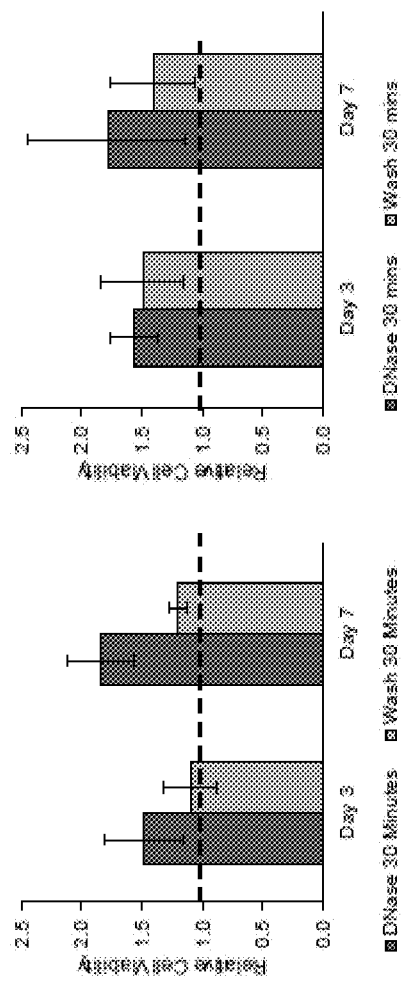
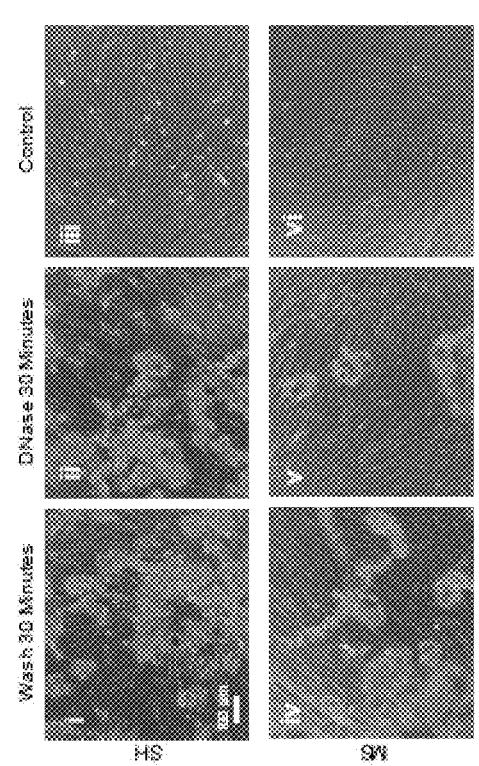
Fig. 14A
Fig. 14B
Fig. 14C

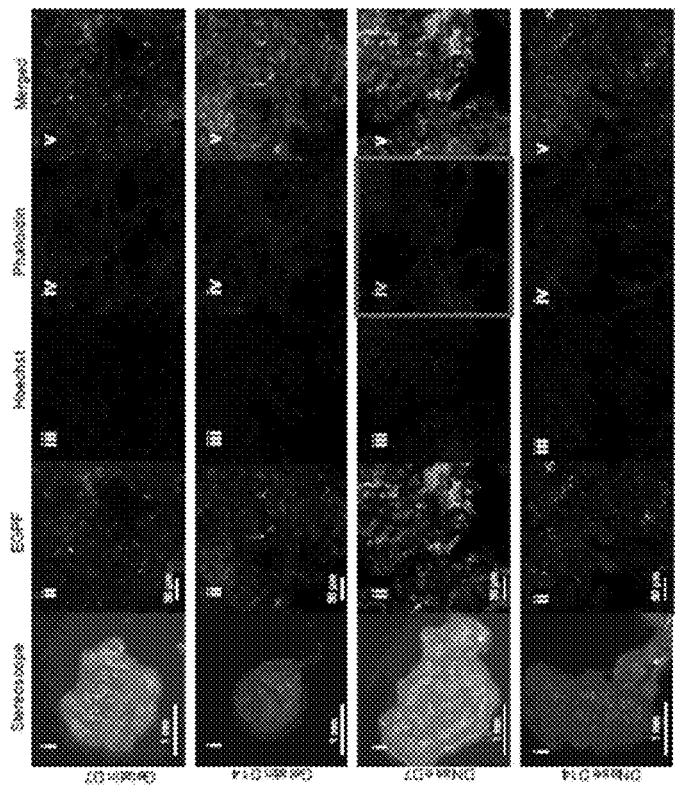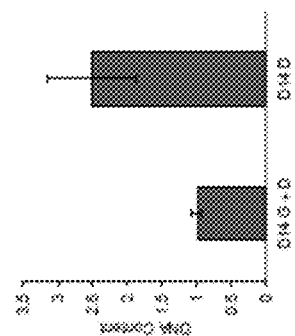
Fig. 15A
Fig. 15B

DECELLULARIZATION OF PLANT CELL CULTURE MATERIALS FOR TISSUE ENGINEERING AND DRUG DELIVERY

CROSS-REFERENCE TO RELATED APPLICATION

This application claims the benefit of the following U.S. Provisional Application No. 62/721,371, filed Aug. 22, 2018, the entire contents of which are incorporated herein by reference.

TECHNICAL FIELD

The disclosure relates generally to materials for use as tissue engineering scaffolds, and methods of preparing such compositions.

BACKGROUND

Bioactive scaffolds have been used in many tissue engineering disciplines in an effort to enhance and direct cellular responses and regeneration. Various factors contribute to cellular responses and regeneration and are often directed by signalling molecules. Natural macromolecules have been a source for scaffolds as they offer many benefits, including but not limited to, lower immune reactivity, tunable degradation rates, and a stronger resemblance to the body's natural structures. Materials such as collagen, fibrin, and silk, have been demonstrated to support cellular regeneration, such as in ligament and tendon repair, bone regeneration, and articular cartilage repair. However, application of these materials has been shadowed with concerns regarding pathogen transmission and reproducibility across mammalian and insect sources.

Decellularization further enhances biocompatibility of cell derived scaffolds by reducing nucleic acid material concentrations and thus lowering incidence of rejection while preserving scaffold structure. Many decellularization techniques require post modification that utilizes degrading substances to remove DNA content at the cost of damaging the scaffold's structure (such as mechanical decellularization through freeze thawing) or by creating a non-biocompatible environment (such as utilizing bleaching components for chemical decellularization).

Accordingly, current methods for preparing scaffolds suffer from a number of shortcomings, such as, lack of biocompatibility, requiring the use of solvents that are not environmentally friendly, and being expensive to engineer. Accordingly, there is still a need for a reliable process for producing biocompatible and bioactive scaffolds.

SUMMARY

In some embodiments, the present disclosure provides methods for altering readily-available biomaterial to carry different proteins, that can be used as a scaffold for growing cells or for drug delivery overcoming limitations of minimally bioactive materials.

In an aspect of the present disclosure, a method for decellularizing cells is provided that includes contacting modified plurality of cells with a composition comprising a nuclease, thereby decellularizing the plurality of cells, wherein the plurality of cells are cellulose producing cells. In some embodiments, the nuclease is DNaseI. In some embodiments, the plurality of cells are plant cells. In some embodiment, the method also includes culturing the plurality of cells prior to contacting the cells with the enzyme that cleaves nucleic acid. In some embodiments, the method also includes isolating cellular material from the cultured plurality of cells.

Another aspect of the present disclosure provides a scaffold that includes decellularized cells derived from a cellulose producing organism and a bioactive molecule. In some embodiments, the bioactive molecule is attached to the decellularized cells. In some embodiments, the decellularized cells are enzymatically decellularized plant-derived cells. In some embodiments, the bioactive molecule is VEGF, bFGF, IL-2, or a molecule that directs mammalian cell expansion, differentiation, or a cellular response. In some embodiments, the decellularized cells are cultured cells.

Another aspect of the present disclosure provides an enzymatically decellularized cell derived from a cellulose producing organism having a bioactive molecule. In some embodiments, the cell is a cultured cell. In some embodiments, the cellulose producing organism is a plant.

Another aspect of the present disclosure provides a method of producing a biocompatible scaffold, and the method includes contacting cellulose producing cells with a composition comprising a nuclease; and creating a scaffold from the decellularized cells. In some embodiments, the method also includes modifying the cellulose producing cells to express a bioactive agent. In some embodiments, the bioactive agent is imbedded, attached, or associated with the cell walls of the cellulose producing cells. In some embodiments, the plurality of cellulose producing cells are cultured cells. In some embodiments, the nuclease is DNaseI. In some embodiments, the composition comprising an enzyme also includes trypsin, collagenase, lipase, dispase, thermolysin, and α-galactosidase.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 4A is an image of BY-2 material after lyophilization that maintains a powdery texture. FIG. 4B is a scanning electron microscope (SEM) 250× image of BY-2 material after 30 minutes of DNase treatment. FIG. 4C is an SEM 2000× image of BY-2 material after 30 minutes of DNase treatment. FIG. 4D is an SEM 250× image of 30-minute wash control treated BY-2 material. FIG. 4E is an SEM 2000× image of 30-minute wash control treated BY-2 material. The circled areas in FIGS. 4C and 4E denote the beads found on the surface of the cell wall material on both the DNase and wash-treated samples.

FIG. 5A is a graph depicting relative DNA content after a 30-minute DNase treatment and after a 30-minute control wash normalized to a negative treatment control. FIG. 5B is a graph depicting relative protein concentration after a 30-minute DNase treatment and after a 30-minute control wash normalized to a negative treatment control;

FIGS. 7A and 7B depict 30-minute vs overnight DNase treatment effects on BY-2 cell derived matrices. FIG. 7A is a graph depicting relative DNA content after a 30-minute or overnight DNase treatment or control wash. FIG. 7B is a graph depicting relative protein concentration after a 30-minute overnight DNase treatment or control wash;

FIG. 9A is a graph depicting relative DNA content in a BY-2 cell-derived matrix cultured in SH media after treatment with different dilutions of DNAse. FIG. 9B is a graph depicting relative DNA content in a BY-2 cell-derived matrix cultured in MS media after treatment with different dilutions of DNAse;

FIG. 10A is a stereoscope image of untreated whole grain rice cell after lyophilization. FIG. 10B is a graph depicting relative DNA concentration of crush rice cells after DNase or wash treatment for 30 minutes. FIG. 10C is a stereoscope image of untreated crushed rice cells after lyophilization. FIG. 10D is a graph depicting protein retention of crush rice cells after DNase or wash treatment for 30 minutes;

FIG. 12A is an image of processed hairy roots. FIG. 12B is a graph depicting DNA retention after decellularization treatment with DNase solution versus wash, normalized to a negative treatment control. FIG. 12C is a graph depicting protein retention after decellularization treatment, normalized to a negative treatment control;

FIGS. 14A, 14B, and 14C depict monolayer fibroblast responses. FIG. 14A is a graph depicting relative SH cell viability at day 3 and day 7 after a 30-minute DNase treatment or control wash. FIG. 14B is a graph depicting relative MS cell viability at day 3 and day 7 after a 30-minute DNase treatment or control wash. FIG. 14C includes images of SH and MS cells after a 30-minute wash or a 30-minute DNase treatment and control;

FIGS. 15A and 15B depict three dimensional aggregate cultures. FIG. 15A includes images showing that hFFs grew throughout the BY-2 cell material aggregate both in the gelatin coated and noncoated aggregates. FIG. 15B is a graph depicting DNA content of BY-2 cell derived matrix aggregates with seeded hFFs normalized to day 7.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present disclosure discusses a method for producing bioactive tissue engineering scaffolds. While scaffolds have been described previously, the present disclosure represents the first instance of using cultured cellulose-producing cells as source cells and an enzymatic decellularization process. In some embodiments, the present disclosure provides decellularized plant cells. In some embodiments, the cells may be modified to express desired proteins or growth factors prior to decellularization. In some embodiments, the present methods use deoxyribonuclease (DNase) or a similar enzyme to decellularize a plurality of cells, which may enable reducing the number of steps and harsh solutions needed for decellularization while also assisting in the retention of proteins expressed by plant cells. As used herein, "plurality of cells" refers to two or more cells. The cells can be the same type of cell (i.e., from the same source) or different types of cells. The decellularized material can be utilized for drug and/or protein delivery and particle for cell expansion. The decellularized material can also incorporate other biomaterial scaffolds (i.e., silk fibroin, collagen, PLGA, fibrin, etc.) to add additional functionality to the biomaterial tissue.

Processing Steps

Figure 1:
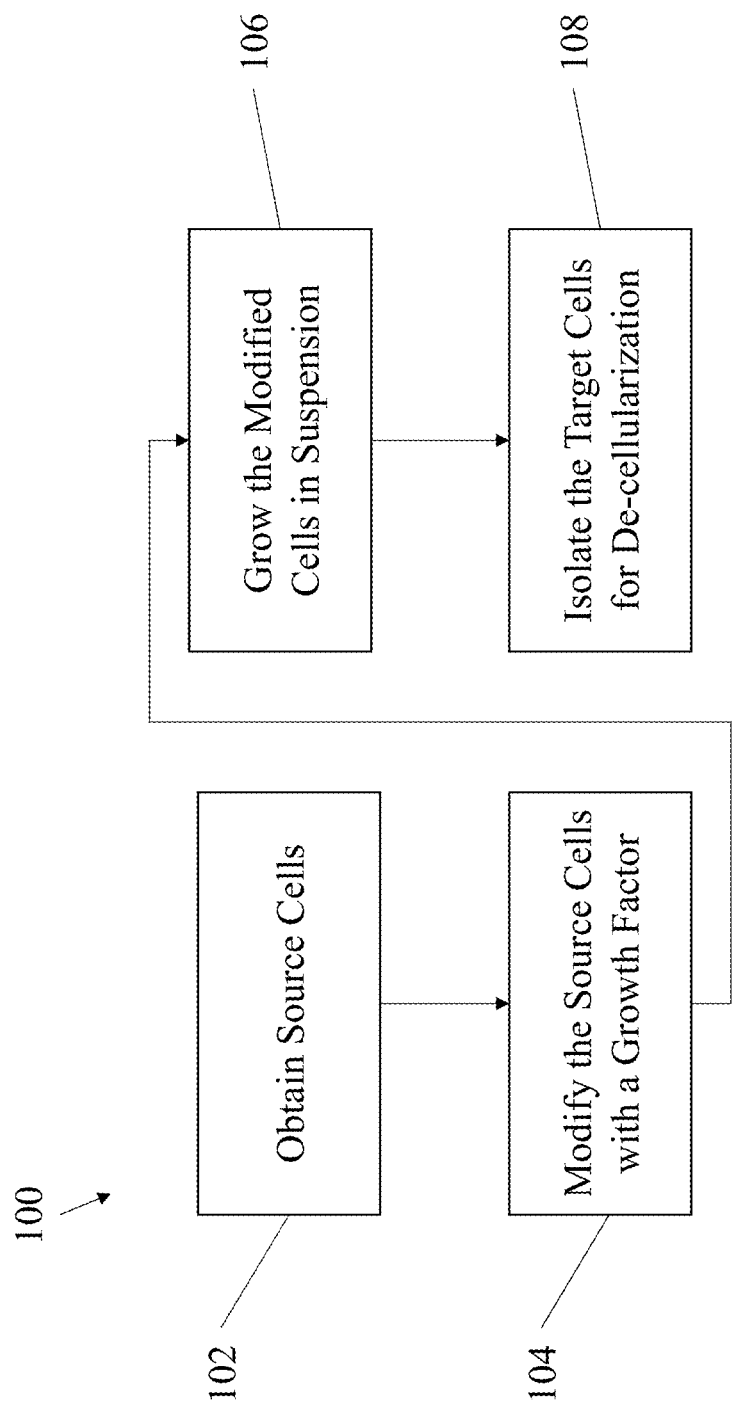
FIG. 1 depicts example processes for preparing modified, decellularized cells.
Figure 2:
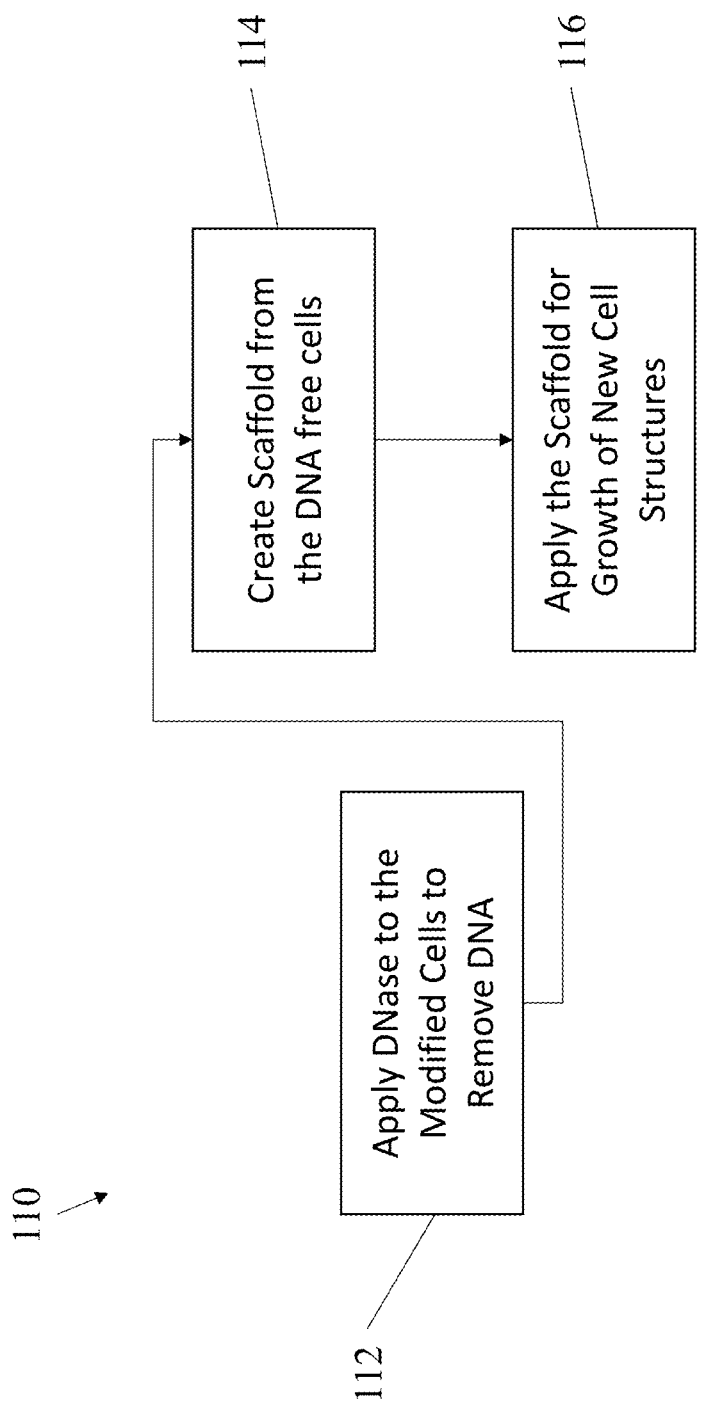
FIG. 2 depicts example processes for preparing modified, decellularized cells.

FIG. 1 and FIG. 2 depict example processes 100 and 110 for preparing modified, decellularized cells of the present disclosure. At step 102 source cells are obtained and isolated from a source material. At step 104, the source cells can be modified/transformed to express a desired bioactive molecule. At step 106, the modified cells are cultured in suspension. At step 108, the modified cells can be isolated and may be stored. At step 112, the modified cells can be treated to decellularize the cells by destroying the genetic material within the modified cells. At step 114, scaffolding can be created from the genetically cleaned cellular material. At step 116, the scaffold can be utilized to grow new cellular structures, such as for tissue engineering or drug delivery applications. The steps provided in FIGS. 1 and 2 are discussed in greater detail below.

Source Cells

The present methods can utilize different source cells. In some embodiments, the source cells may be derived from cellulose-producing organisms. A variety of organisms, such as plants, algae, fungi, protists, and bacteria, produce cellulose and thus can be employed as a source for cells. In some embodiments, the cells obtained from the source ("source cells") are plant cells. From a manufacturing standpoint, plant cultures provide a readily available and cost-effective biomaterial source that does not require post processing with hazards and volatile solvent while retaining tuneable biomarkers for mediated cell response. Furthermore, plant cultures have not been shown to contain known human pathogens or bacterial endotoxins. Methods of the present disclosure can utilize cells from tobacco leaves, rice leaves, hairy roots, or any other combination of leaves, stems, seeds, and cotyledons of plant species. In some embodiments, other commonly cultured plant materials, such as, for example, carrots (stem), *Arabidopsis*, lettuce, or medicinal plants can be used. Undifferentiated plant cells can be isolated from cellulose-producing organisms using any combination of known plant callus induction procedures and plant tissue culture methods known in the art.

In some embodiments, mammalian cells can be utilized with the present disclosure. For example, mammalian cells, green microalgae (e.g., *Chlamydomonas reinhardtii*), yeasts, (e.g., *Saccharomyces cerevisiae, Pichia pastoris*, etc.), bacteria of the genera *Acetobacter, Sarcina ventriculi, Agrobac-*

*terium*, etc. can be utilized with the disclosed methods and systems. The bacteria of the genera *Acetobacter, Sarcina ventriculi*, and *Agrobacterium* can be used to create a bulky matrix of cellulose while the green microalgae may not produce a cellulose matrix in which they grow in.

Genetic Modification

In some embodiments, source cells can be genetically modified to express desired bioactive molecules, such as growth factors. In some embodiments, the bioactive molecules are non-covalently attached to the cells. For example, plant cells (e.g., BY-2 plant cells) can be genetically engineered (e.g., using an *Agrobacterium*-mediated method), to express VEGF, bFGF, IL-2, or other molecules that direct mammalian cell expansion, differentiation, and other desired cellular responses in culture systems. Other types of proteins can be utilized with the present disclosure, for example, proteins such as cytokines, antibodies, enzymes, receptors, etc., can be expressed by plant cells. Similarly, other transformation techniques can be utilized, including but not limited to particle bombardment or any other cell transformation methods that introduce DNA into virtually any cell type. In some embodiments, the bioactive agent is imbedded, attached, or associated with the cell well of the source cells prior to and/or after decellularization.

In some embodiments, modified cells expressing the bioactive molecule can be cultured in a culture medium for a predetermined period of time. After the cells have been sufficiently cultured, the cells can be isolated from the culture media and stored for further processing. For example, the modified cells can be isolated by passing the culture through Whatman filter paper or microfiltration membrane. In some embodiments, the modified cells can be harvested by centrifugation at 3000×g for 5-10 minutes. In some embodiments, the modified cells can be lyophilized for storage.

In some embodiments, the source cells are not genetically modified. In some embodiments, the source cells or scaffold are labelled or otherwise interact with a bioactive agent. In some embodiments, the bioactive agent is deposited onto the source cells or onto the resulting scaffold. For example, in some embodiments, a bioactive agent may be a protein that can bind to or otherwise interact with the cell wall of the source cells.

Decellularization

In some embodiments, the modified cells are decellularized. In some embodiments, the decellularization technique is selected such that the cells are decellularized by at least 60% compared to untreated cells and elicit minimal cytotoxic and inflammatory response in in vitro culture. In some embodiments, the cells are about 94 to about 98% decellularized. In some embodiments, the cells are about 99 to about 100% decellularized. In some embodiments, the cells are 90%-95%, 95%-98%, 98%-99%, or 99%-100% decellularized, depending on a desired approach. In some embodiments, the cells may retain at least about 20% to about 40% of the bioactive molecule. In some embodiments, the cells may retain at least about 90% of the bioactive molecule.

In some embodiments, the modified cells can undergo an enzymatic treatment. For example, suitable enzymes include, but are not limited to, nucleases, including deoxyribonucleases and ribonuclease, trypsin, collagenase, lipase, dispase, thermolysin, and α-galactosidase. Nucleases, such as exodeoxyribonucleases, endodeoxyribonucleases, endoribonucleases, and exoribonucleases can be used decrease or remove nucleic acid content in the modified cells. In some embodiments, the exodeoxyribonucleases, endodeoxyribonucleases, endoribonucleases, and exoribonucleases are used in combination with deoxyribonuclease (DNase). In some embodiments, the modified cells can be treated with DNase. DNase I is a nuclease that preferentially cleaves DNA at phosphodiester linkages adjacent to a pyrimidine nucleotide. DNase II, which functions optimally at a low pH (e.g., the pH in the lumen of a lysosome), is another example of a DNA endonuclease. Other nucleases are contemplated herein.

In some embodiments, the isolated plant cell material can be treated with either a 0.001 mg/mL to 1 mg/mL DNase in phosphate buffer saline (PBS) with calcium and magnesium solution to remove any genetic material. In some embodiments, PBS can also be used. In some embodiments, the buffer can be any buffer having a neutral pH. In some embodiments, the buffer can be any buffer having a pH (pKa 4-8) can be used, such as piperazine-N,N'-bis(2-ethanesulfonic acid) (PIPES), 3-(N-morpholino)propanesulfonic acid (MOPES), 4-(2-hydroxyethyl)-1-piperazineethanesulfonic acid (HEPES), 2-(N-morpholino)ethanesulfonic acid (MES), tris(hydroxymethyl)aminomethane (TRIS), etc.

In some embodiments, the enzyme (e.g., a DNase) solution concentration can be dependent on the enzymatic activity, the materials being decellularized, etc. In some embodiments, the range of the DNase concentration can be about 0.001 mg/mL to 5 mg/mL. In some embodiments, the range for the DNase concentration can be about 0.025 mg/mL to 5 mg/mL, about 0.05 mg/mL to 5 mg/mL, about 0.075 mg/mL to 5 mg/mL, about 0.10 mg/mL to 5 mg/mL, about 0.2 mg/mL to 5 mg/mL, about 0.3 mg/mL to 5 mg/mL, about 0.4 mg/mL to 5 mg/mL, about 0.5 mg/mL to 5 mg/mL, about 0.6 mg/mL to 5 mg/mL, about 0.0.7 mg/mL to 5 mg/mL, about 0.8 mg/mL to 5 mg/mL, about 0.9 mg/mL to 5 mg/mL, about 1.0 mg/mL to 5 mg/mL, about 1.5 mg/mL to 5 mg/mL, about 2 mg/mL to 5 mg/mL, about 2.5 mg/mL to 5 mg/mL, about 3 mg/mL to 5 mg/mL, about 3.5 mg/mL to 5 mg/mL, about 4 mg/mL to 5 mg/mL, or about 4.5 mg/mL to 5 mg/mL. In some embodiments, the range for the DNase concentration is about 0.025 mg/mL to 4.5 mg/mL, about 0.25 mg/mL to 4 mg/mL, about 0.025 mg/mL to 3.5 mg/mL, about 0.025 mg/mL to 3 mg/mL, about 0.025 mg/mL to 2.5 mg/mL, about 0.025 mg/mL to 2 mg/mL, about 0.025 mg/mL to 1.5 mg/mL, about 0.025 mg/mL to 1 mg/mL, about 0.025 mg/mL to 0.9 mg/mL, about 0.025 mg/mL to 0.8 mg/mL, about 0.025 mg/mL to 0.7 mg/mL, about 0.025 mg/mL to 0.6 mg/mL, about 0.025 mg/mL to 0.5 mg/mL, about 0.025 mg/mL to 0.4 mg/mL, about 0.025 mg/mL to 0.3 mg/mL, about 0.025 mg/mL to 0.2 mg/mL, or about 0.025 mg/mL to 0.1. In some embodiments, the range for the DNase concentration can be about 1 mg/mL to 2.0 mg/mL.

In some embodiments, the modified cells can be decellularized using a physical treatment, such as temperature cycling (e.g., freeze/thaw) force and pressure, electrical disruption, or supercritical carbon dioxide. Other methods for cell isolation can also be used, for example, chemical treatment (e.g., surfactants such as t-octyl phenoxy polyethoxy ethanol (triton X-100), tridecyl polyethoxy ethanol (ATE), sodium docecyl sulfate (SDS), sodium deoxycholate, CHAPS, etc). The cell isolation can also utilize a chelating agent such as ethylenediaminetetraacetic acid (EDTA), diethylenetriaminepentaacetic acid (DTPA).

The cell material resulting from the decellularization process can include a cellular structure (e.g., cellulose or a cell wall) with an imbedded, attached, or associated bioactive molecule provided in the cellular modification process.

Applications

The bioactive decellularized material can be utilized for a variety of applications. For example, the material can be utilized to create a scaffold for tissue engineering, drug delivery and pharmaceutical testing. In some embodiments, because the decellularized material also retains substantial amounts of bioactive molecules after decellularization, it may be manipulated into a functionalized biomaterial for mammalian cultures. In some embodiments, the resulting functionalized biomaterial provides a three-dimensional environment for cell culture that retains bioactive molecule and is biocompatible. In some embodiments, the functionalized biomaterial can be fabricated into microparticles for cell expansion in bioreactors or into scaffolds for tissue engineering or regeneration and can be applied to mammalian cell populations such as endothelial cells, fibroblasts, or T cells.

In some embodiments, the scaffold has a bioactive molecule associated with it. In some embodiments, the bioactive molecule is expressed in the cells prior to decellularization (e.g., in cells genetically modified to express the bioactive molecule). This bioactive molecule, once expressed, can be attached, imbedded, or otherwise associated with the cell wall and is retained in the scaffold after decellularization of the cells. In some embodiments, the bioactive molecule is added to the scaffold after decellularization of the source cells. For example, a bioactive molecule may be deposited, attached, imbedded, or otherwise associated with the scaffold as described above.

As a drug delivery system, decellularized matrices are used to leach a functional protein or a variety of proteins into the space surrounding the scaffolds. This method provides multiple avenues of drug delivery through oral, injection, and material embedded modalities. In some embodiments, cellulase can be applied to the scaffold material to dissociate the remaining cellulose from the plant derived material while maintaining protein retention. In some embodiments, a C-terminal glycosylphosphatidylinositol or glycophosphatidylinositol (GPI) anchor or cellulose binding domain may be appended to the designer molecules.

In some embodiments, 3D scaffolds systems are produced from the decellularized material that provides the frame work for applications in vascular, neuronal, or respiratory tissue production and regeneration. The combination of tunable protein secretion, significant DNA removal, and aggregate culmination allows for the formation of tunable tissue engineered scaffolds that can be manipulated to suggest various types of cellular response.

Examples, which are set forth below to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the embodiments of the present disclosure, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for.

EXAMPLES

BY-2 transformation and culture. Tobacco Bright Yellow-2 (BY-2) cells expressing $(SP)_{32}$-EGFP were transformed using an *Agrobacterium*-mediated method, then cultured in either Schenk and Hildebrandt medium (SH) or Murashige and Skoog (MS) basal media, both containing 2.1 mg/L p-cholorphenoyacetic acid, 0.4 mg/L 2,4-dicholorphenoxyacetic acid(2,4-D), 0.1 mg/L kinetin, and 34 g/L sucrose (kindly provided by Dr. Jianfeng Xu). The cells were cultured in media suspension incubated at 23° C. in shaker flasks rotating at 95 rpm for 7 days. Afterwards, the plant cell material was isolated by vacuum filtration through Whatman filter paper, then washed three times with sterile distilled water. The BY-2 cell material was stored at −80° C. until further processing.

Rice cell transformation and culture. Rice cells (*Oryza sativa*) expressing EGFP (driven by the ubiquitin promoter) were generated via particle bombardment. The transformed rice cells were then maintained in N6 medium containing 10 mg/L myo-inositol, 0.38 g/L Hy-Case® SF Casein acid hydrolysate, 2.88 g/L proline, 2.1 mg/L p-chlorophenoxyacetic acid, 0.4 mg/L 2,4-dichlorophenoxyacetic acid (2,4-D), 0.1 mg/L kinetin, and 30 g/L sucrose. The cells were cultured in suspension using shaker flasks rotating at 95 rpm at room temperature (23° C.) for 21 days. The cultured cells were then harvested by vacuum filtration through Whatman filter paper, washed three times with sterile distilled water, and stored at −80° C. until further processing.

Generation of transgenic hairy roots. Transgenic hairy roots expressing $(SP)_{32}$-EGFP (driven by the CaMV 35S promoter) were generated by infecting young leaves of the transgenic tobacco (*Nicotiana tabacum*) plantlets with *Agrobacterium rhizogenes* (ATCC 15834). The obtained hairy roots were maintained in solid SH medium containing 34 g/L of sucrose without supplementation of plant growth regulators. The transgenic hairy roots were then cultured in liquid SH medium in shaker flasks rotating at 90 rpm at room temperature (23° C.) for 12 days. The cultured root tissues were harvested by vacuum filtration, washed three times with sterile distilled water, and stored at −80° C. until further processing.

Figure 3:
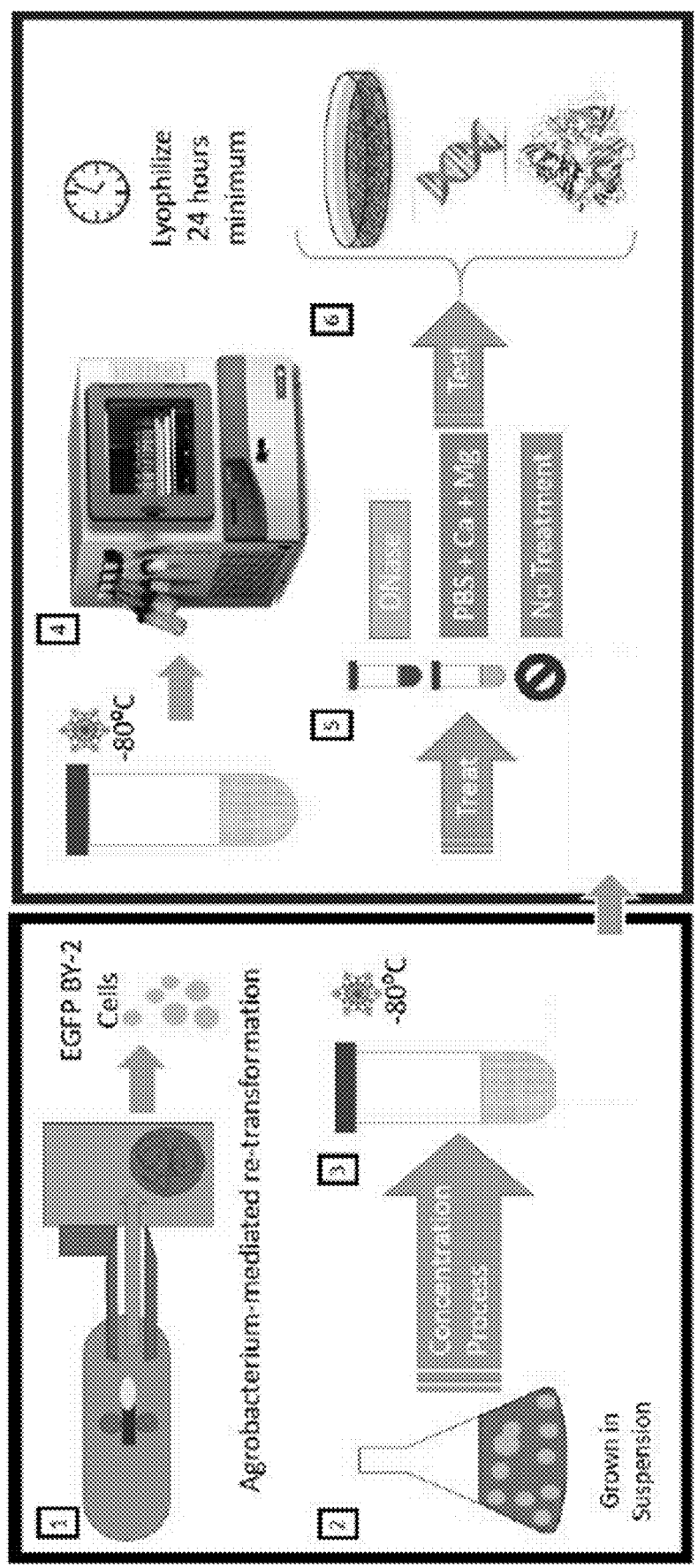
FIG. 3 depicts a decellularization process of BY-2 plant material. "EGFP" denotes enhanced green fluorescent protein.

Decellularization of BY-2 cell derived matrices. FIG. 3 illustrates the decellularization process. More specifically, step 1 shows that BY-2 cells are transformed using an *Agrobacterium* method to modify them to express $(SP)_{32}$-EGFP protein. Step 2 shows that the cells are then cultured in suspension for 7 days in either SH or MS media using a shaker flask rotation at 95 rpm. Step 3 illustrates the plant cell material being isolated by passing the culture through Whatman filter paper, then being frozen at −80° C.

Decellularization of BY-2 cell derived matrices. Step 4 illustrates the BY-2 material being lyophilized for 24 hrs and then stored at room temperature. Step 5 shows that the BY-2 material is then treated with either a 1 mg/mL DNase in PBS+$Ca^{2+}$+$Mg^{2+}$ solution, in PBS+$Ca^{2+}$+$Mg^{2+}$, or with no treatment. Step 6 shows that the samples are then analyzed for biocompatibility, DNA content, or protein content.

Frozen BY-2 cells were mechanically decellularized through lyophilization (Labconco, Kansas City, Mo.) for 24 h. The samples were then removed and kept at room temperature until chemical decellularization processing. The lyophilized BY-2 cell material (2 mg) was chemically decellularized using 0.5 mL of 1 mg/mL DNase in PBS containing $Mg^{2+}$ and $Ca^{2+}$ (Sigma, Saint Louis, Mo.). Trapped air was released from the samples by degassing for 5 mins. Samples were then incubated at 37° C. for 30 min or 12 h. Following incubation, the samples were washed 4 times with 0.5 mL of PBS and centrifuged at 14,000 rpm for 5 min each time at room temperature. For DNase titration studies, serial dilutions of DNase solution (2-0.0025 mg/mL) were employed to treat the lyophilized BY-2 cell material for 30 mins, followed by the aforementioned washing procedure. Rice cells and hairy roots were decellularized following an identical procedure using 0.5 mL of 1 mg/mL DNase in PBS containing $Mg^{2+}$ and $Ca^{2+}$ for 30 min at 37° C.

DNA analysis. Samples were analysed for DNA retention post treatment using a Quant-iT™ PicoGreen® dsDNA assay kit (Invitrogen, Carlsbad, Calif.) following the manufacturers protocol. First, the samples incubated with 0.5 mL of 125 µg/mL Papain digest (Worthington Biochemical Corp., Lakewood, N.J.) with 100 mM sodium phosphate buffer containing 10 mM $Na_2$ EDTA (PBE) and 11.1 mM L-cysteine for 16 h at 60° C. After incubation, the samples were centrifuged and the supernatant collected and diluted 1:10 with 1× Tris-EDTA (TE) buffer. The samples were incubated at room temperature for 5 min in a 200-fold dilution of the PicoGreen® dye in TE buffer. The DNA concentration was determined by measuring the fluorescence at an excitation of 480 nm and emission of 520 nm (Victor Multilabel Plate Reader, Perkin Elmer, Waltham, Mass.) and comparing to standard curve of lambda DNA (0 µg/mL to 2 µg/mL). Sample groups were (1) DNase treated, (2) ash controls, and (3) lyophilized.

Protein quantification. Protein retention was quantified using a Pierce™ bicinchoninic acid (BCA) assay kit (ThermoScientific, Rockford, Ill.). The samples were solubilized in 6 M guanidine hydrochloride for 16 h at room temperature. Next, the samples were spun down at 14,000 rpm for 5 min. The supernatant was removed and combined with BCA solution in a 1:1 ratio, then incubated for 30 min at 37° C. The protein concentration was determined by measuring the absorbance at 562 nm (Spectra Max 250, Molecular Devices, San Jose, Calif.) and comparing to a standard curve of bovine serum albumin (0 µg/mL-2,000 µg/mL). Sample groups were (1) DNase treated, (2) washed with PBS containing Mg and Ca, and (3) lyophilized.

Western blotting. For extracting intracellular proteins, treated and non-treated plant cells and hairy root tissues were ground by mortar and pestle in SDS extraction buffer (150 mM Tris-HCl, pH 6.8, 30% glycerol, 6% SDS, 5 mM EDTA) at a ratio of 1:2 (w/v). Samples were centrifuged at 13,000×g and 4° C. for 15 min and the supernatants were collected for an anti-EGFP Western blotting assay. Samples and EGFP standard (BioVision Inc., CA) were separated on a 10% Tris-HCl mini gel (Bio-Rad, CA). After electrophoresis, proteins were electro-blotted onto a 0.2 µm nitrocellulose membrane (Bio-Rad, Hercules, Calif.). Protein blots were blocked with 3% (w/v) BSA in Tris-buffered saline buffer (pH 7.5) containing 0.1% Tween® 20 for 1.0 hr at room temperature. Immunoblot detection of EGFP was carried out using a rabbit-anti EGFP antibody (ThermoFisher Scientific Inc., MA) as primary antibody and an IRDye® 680RD goat anti-rabbit IgG (H+L) (Li-Cor Biosciences, NE) as secondary antibody. The images were captured on the Li-Cor Odyssey Fc imaging system (Li-Cor Biosciences, NE) and the target proteins were quantified with Li-Cor's Image Studio™ Software.

Fluorescence imaging. The samples were fixed in 4% paraformaldehyde (PFA) (Sigma) for 30 min and then stained for nuclei with 1:600 Hoechst (ThermoFisher Scientific, Waltham, Mass.). Samples containing hFFs were stained with Red Phalloidin (1:500 Abcam, Cambridge, Mass.) in PBS containing 0.2% Triton X-100, then washed with PBS gently before imaging.

Scanning electron microscopy (SEM). SEM images were taken using a JSM-7000F SEM (JEOL, Tokyo, Japan) to evaluate surface morphology of the BY-2 cell-derived material. Samples were mounted on SEM pedestals using copper tape and sputter-coated with gold for 60 s at 25 mA.

Monolayer fibroblast response. Human foreskin fibroblasts (hFFs) were cultured in DMEM supplemented with 10% fetal bovine serum, 1% L-glutamate, 100 U/mL penicillin, and 100 µg/mL streptomycin. hFFs were seeded in a 48-well plate at 20,000 cells per well 24 h prior to treatment. (1) Decellularized or (2) wash-only BY-2 cell-derived material was introduced to each well. Viability was measured on day 1, day 3, and day 7 after material introduction via resazurin metabolic assay (30 µg/mL, Acros Organics, Pittsburgh, Pa.). At each time point, media was removed and 250 µL of resazurin solution was added to each well and incubated at 37° C. for 30 min. The resazurin solution was then removed and the fluorescence measured at excitation of 544 nm and emission of 590 nm. Measurements were background subtracted and normalized to day 1 readings.

Three dimensional aggregate cultures. hFFs were seeded at 55,000 cells per 1.5 mL microcentrifuge tube with 1 mg of 30 min DNase treated BY-2 cell material coated (1) with or (2) without 0.1% gelatine (Sigma) in 375 µL of hFF media. Cells were cultured at 37° C. for 7 and 14 days. To prepare the samples for further analysis after culture, the media was discard and the remaining aggregate material was fixed in 4% PFA for 30 mins, then gently washed once with PBS for further imaging. Aggregates for DNA quantification were frozen at −20° C.

Macrophage response. THP-1 monocytes were plated in 48-well plates at 50,000 cells per well and differentiated to macrophages using 100 ng/mL PMA (Sigma) in RPMI media supplemented with 10% fetal bovine serum, 1% L-glutamate, 100 µg/mL penicillin, and 100 µg/mL streptomycin for 16 h. The media was removed and replaced with 250 µL of RPMI media in which (1) DNase treated or (2) wash-treated BY-2 cell derived material had been allowed to leach in for 72 hours beforehand. Lipopolysaccharide (LPS) derived from $E.\ coli$ (100 ng/mL, Sigma) was used as a positive control and untreated macrophages with fresh RPMI media were used a negative control. Cells were treated for 48 h. Afterwards, the media was collected from each condition and TNF-α concentration was quantified using a TNF-α Standard TMB ELISA Development Kit (Pepro Tech, Rocky Hill, N.J.) according to manufacturer's instructions. Samples were diluted 1:10 using the reagent diluent suggested by the manufacturer protocol to prevent saturation.

Statistics. Absorbance values for protein, DNA, cell viability, and TNF-α quantification were determined as the mean±SD. Statistical significance was determined with a one-way ANOVA test followed by Tukey honestly significance test ($p<0.05$) or with a student's T-test ($p<0.05$) using Microsoft Excel 2016 and GraphPad Prism (version 5.01).

Results

Decellularization with DNase for 30 minutes depleted the DNA content to <2% of the original amount. These plant cell lines are readily amenable to transformation with functional molecules to develop engineering culture models with the ability to control mammalian cell response and function. Enhanced green fluorescent protein (EGFP) was used to confirm protein retention within the plant cell walls after decellularization. DNase treatment decreased the protein level by ~60%. This same effect was observed with buffer-only controls suggesting the reduction is due to leachable protein. Extended treatment with DNase or buffer-only did not facilitate additional protein loss. Similar results for decellularization and protein retention were observed for EGFP-expressing rice cells. Monolayer cultured human foreskin fibroblasts (hFFs) exhibited increased cell viability (as indicated by resazurin assay) upon exposure to the BY-2 cell-derived matrix for 7 days. Additionally, the BY-2 cell-derived matrix permitted hFF attachment in a three-dimensional aggregate model. Overall, these studies demonstrate the effective decellularization of plant cell lines with a positive impact on hFF viability and a novel 3D environment for cell culturing. These decellularized matrixes, coupled with genetic engineering approaches to incorporate function proteins, have promising applications in tissue engineering and drug delivery.

Morphology. The lyophilized plant cells were pulverized through the lyophilization process and exhibited static interactions when handled as is common with materials of similar physical composition. However, once the treated materials were rehydrated and lyophilized again, the material became more of a pellet that could be handled with tweezers, but easily collapsed into its powder form when adequate force was applied.

Figure 4C:
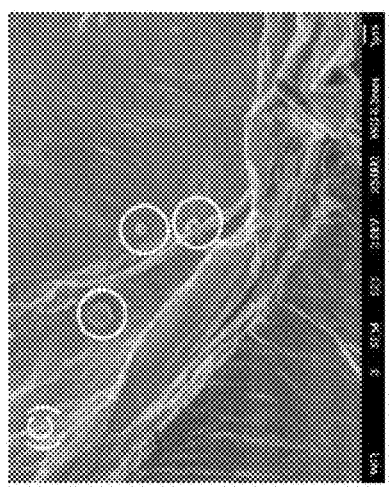
FIGS. 4A-4E depict morphology of BY-2 material post-lyophilization and treatment.
Figure 4E:
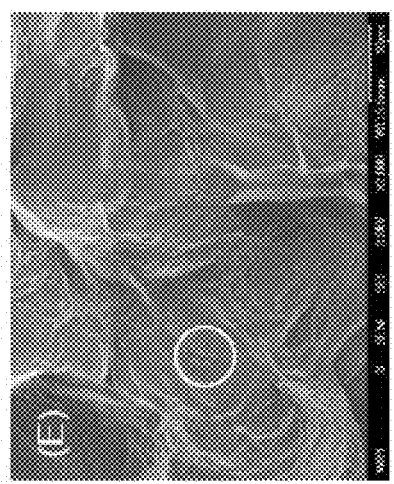
Figure 4B:
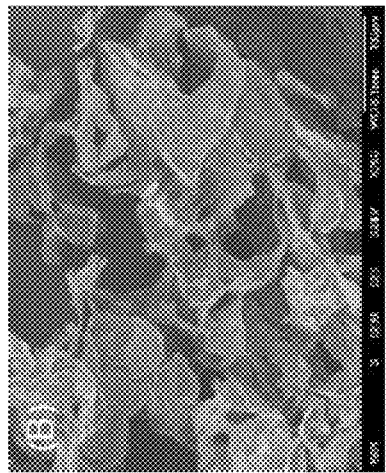
Figure 4D:
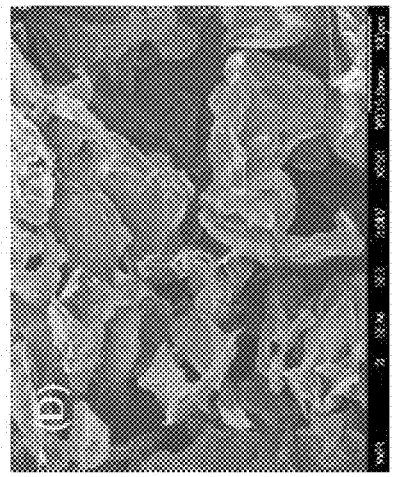
Figure 4A:
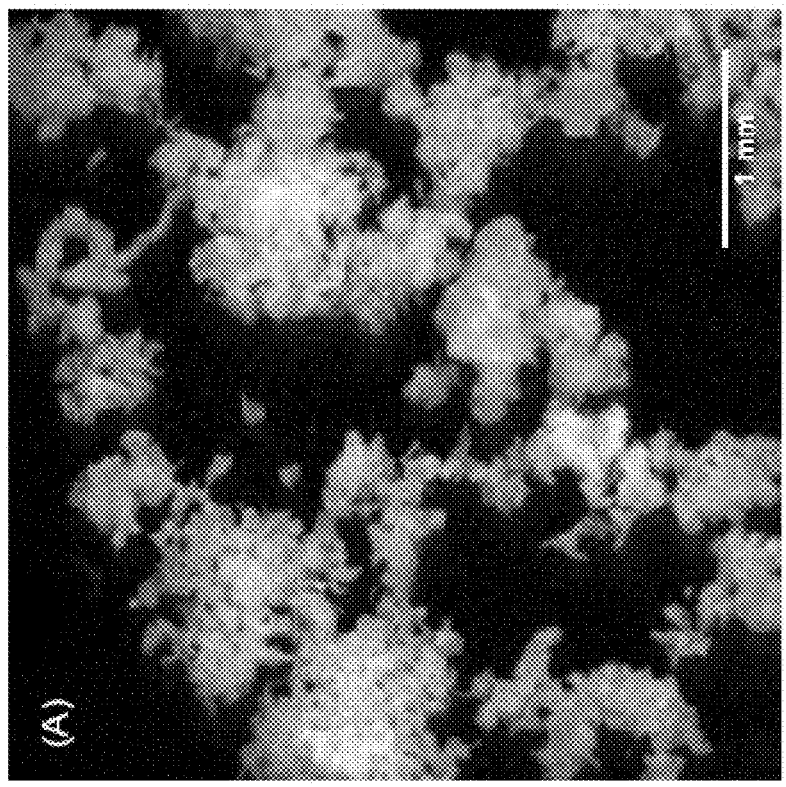

SEM imaging revealed no visible differences in surface morphology between the DNase and wash conditions. Both samples exhibited smooth surfaces and had similar pore sizes. Closer examination revealed similar occurrences of small beads on the surfaces of both treated samples, most notably in the crevices formed by the disrupted cell wall (FIG. 4). FIG. 4A depicts the BY-2 material after lyophilization maintaining a powdery texture. FIGS. 4B and 4C show the SEM image of 30 min DNase treated BY-2 material at 250× and 2000×, while FIGS. 4D and 4E show the SEM image of 30 min wash control treated BY-2 material at 250× and 2000×. The circled areas denote beads found on the surface of the cell wall material on both the DNase and wash-treated samples.

Figure 5B:
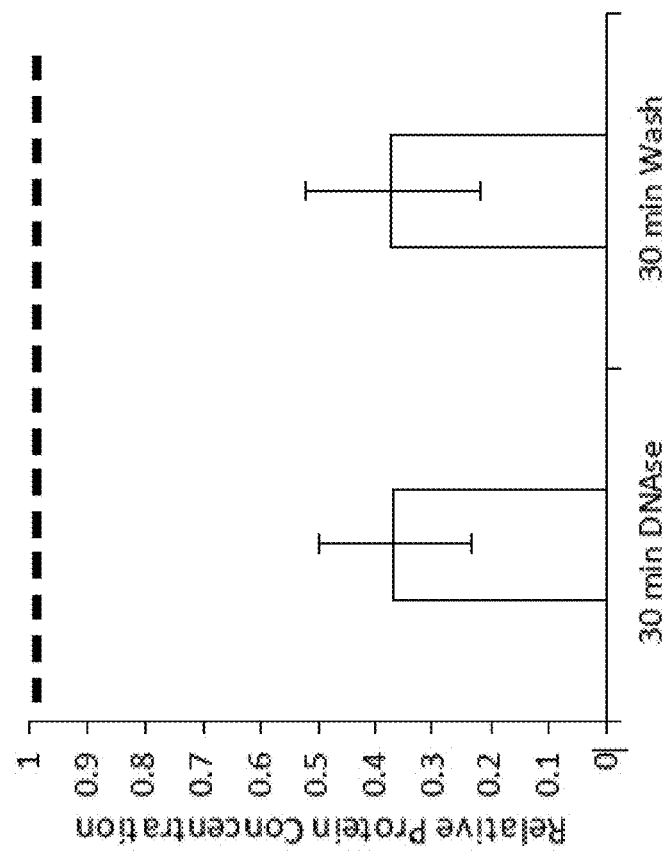
FIGS. 5A and 5B depict biochemical characterization of treated material.
Figure 5A:
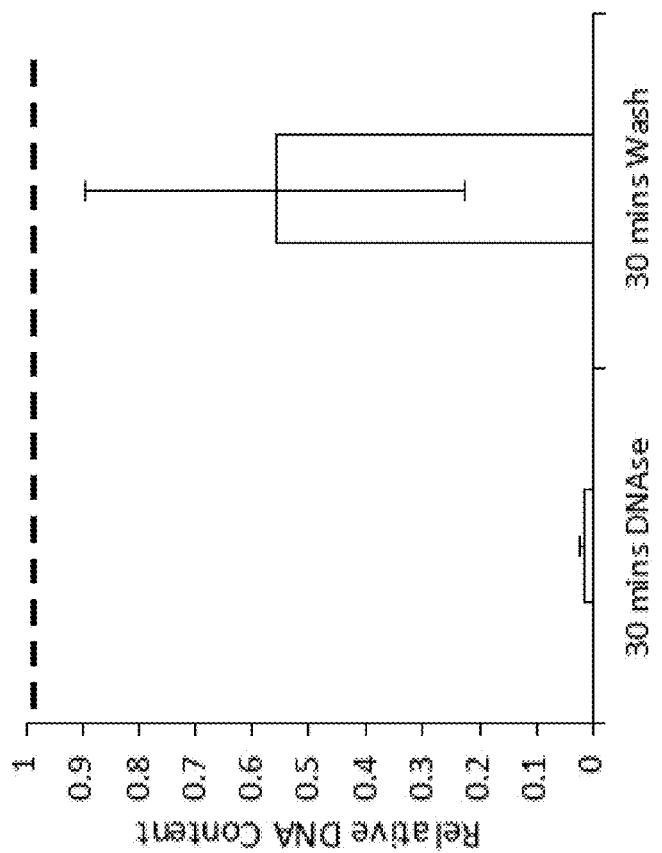

Decellularization of BY-2 cell matrix. Studies were conducted to optimize the duration and concentration of chemical decellularization treatment for removing the maximum amount of DNA possible from the BY-2 plant derived material while retaining significant protein concentration. The studies show that exposing the BY-2 material to a 1 mg/mL solution of DNase solution for 30 mins yielded a dramatic reduction in DNA content by over 90%, as compared to the untreated negative control (FIG. 5A). FIG. 5A depicts the DNA retention after decellularization treatment with DNase solution versus wash. Normalized to a negative treatment control and FIG. 5B depicts the protein retention after decellularization treatment, normalized to the negative treatment control.

Figure 6:
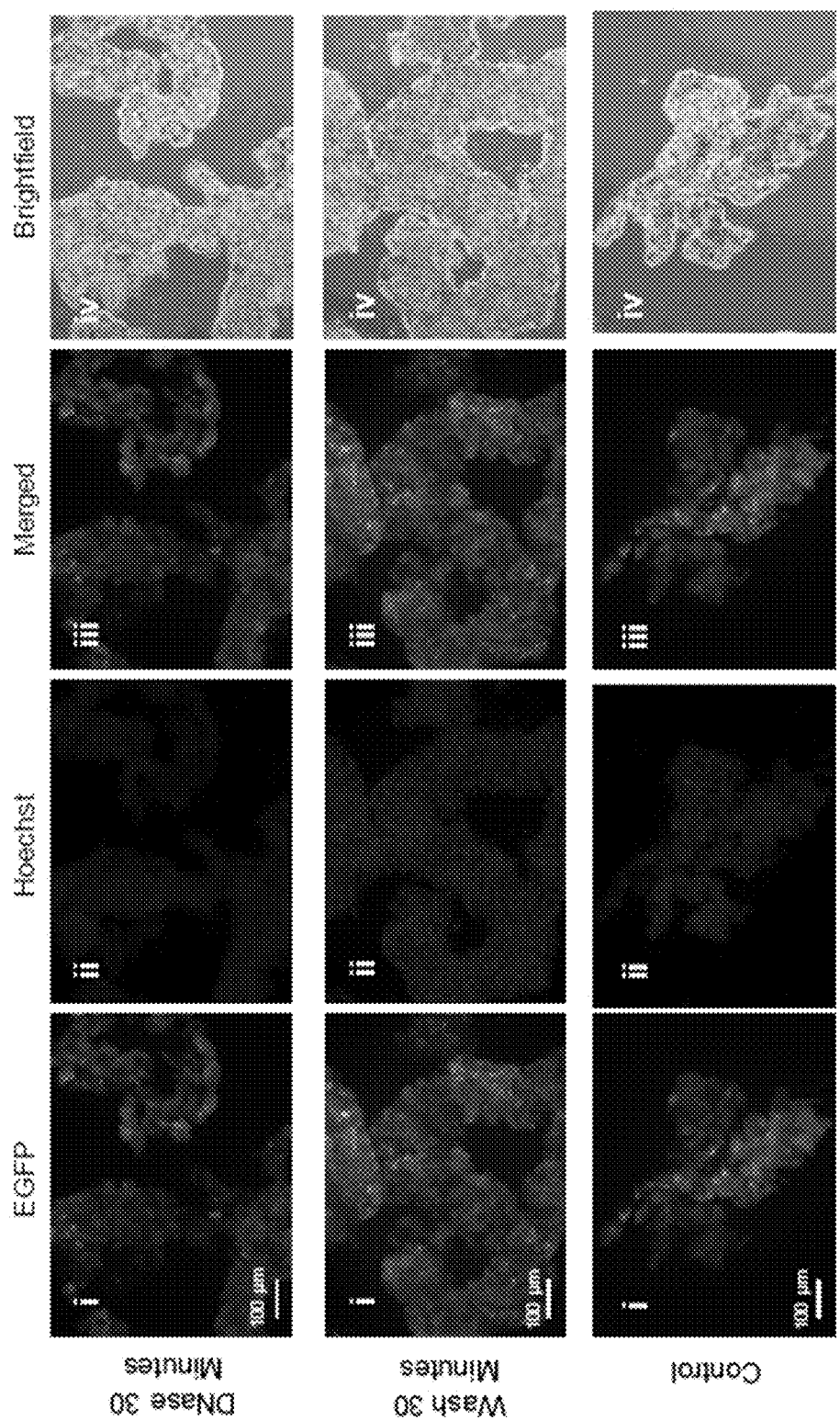
FIG. 6 depicts images of materials after processing.

Additional imaging confirmed the findings as evident by the clear lack of nuclei in the DNase treated materials compared to the wash-treated and negative control groups (FIG. 6). FIG. 6 depicts how the BY-2 derived cellulose structure remains intact after treatment, and retains its EGFP protein within its cell wall (light shading). There is a noticeable difference in nuclear morphology with DNase treatment (lack of punctate staining of Hoechst-labeled DNA) while the wash-treated and control cells retain intact nuclei. Moreover, an approximate 60% reduction in protein content was observed in both DNase and wash-treated samples compared to the negative control (FIG. 5B). There was no significant improvement in DNA reduction or protein retention exposing the material to the DNase solution for longer periods of time (FIG. 7). FIG. 7A shows DNA retention for DNase treated samples for 30 min or overnight in BY-2 derived material cultured in MS media. Overnight treated samples lacked consistent DNA retention levels in the DNase treatment group while the wash-treated group should no statistical significance between the two treatment durations. FIG. 7B shows protein retention for DNase and wash-treated samples for 30 min or overnight in BY-2 derived material cultured in MS media. Again, there was no statistical significance in DNA retention between 30 min of treatment or overnight.

Figure 8:
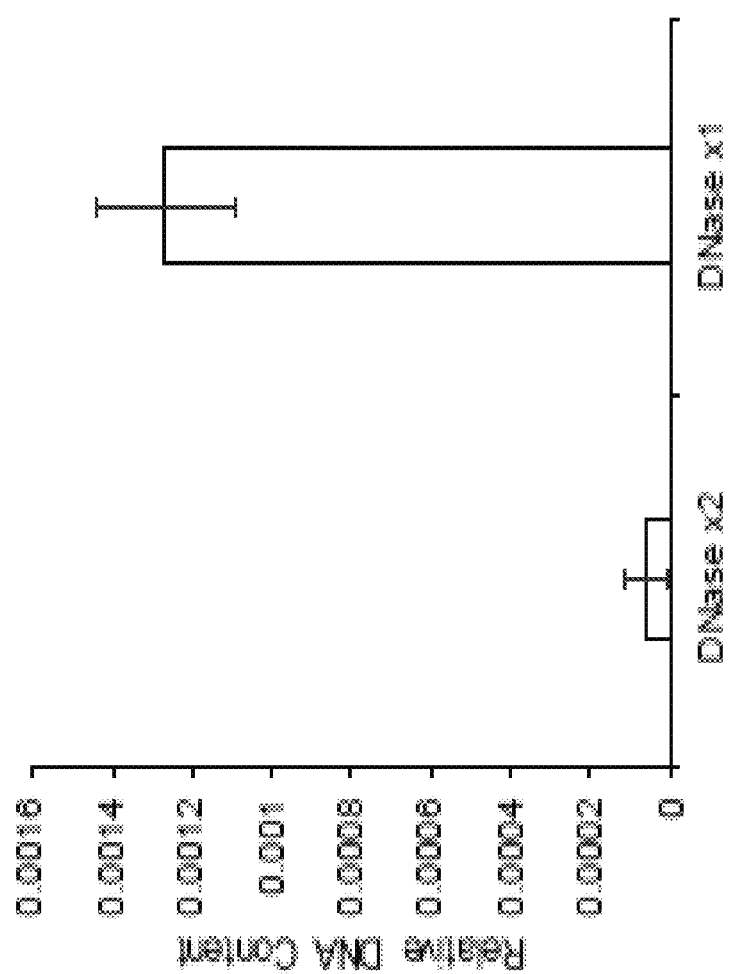
FIG. 8 is a graph comparing results of single and double DNase treatments.

These DNase treatment results suggest that the majority of protein and DNA lost was leached within the first 30 mins of exposure when submerged in aqueous solution. Samples were treated with a 1 mg/mL solution of DNase solution for 15 mins. The treatment solution was removed and replaced with a fresh 1 mg/mL solution of DNase solution and treated for an additional 15 mins. This resulted in further DNA loss (FIG. 8). FIG. 8 shows the 1 mg/mL DNase treatment solution that was removed after 15 min, then replaced with fresh DNase solution. Although less DNA content was seen in the double treated material, the reduction was not dramatic enough to warrant the loss of efficiency and increased material costs that would accompany replacing the treatment solution.

Figure 9A:
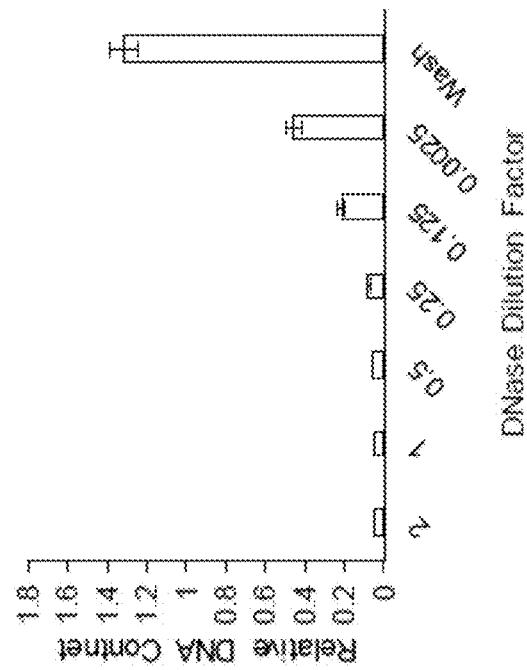
FIGS. 9A and 9B depict results of DNase titrations.
Figure 9B:
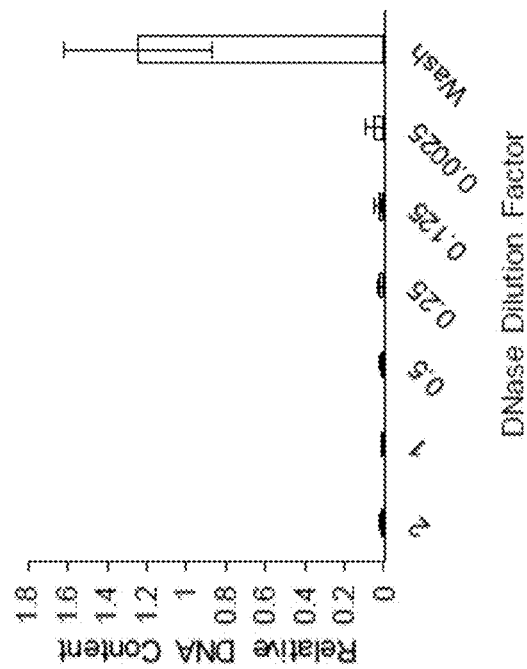

Evaluation of DNase concentration on decellularization process of BY-2 cell-derived matrix. To determine the concentration of DNase solution for optimal DNA removal, a titration study was performed on BY-2 cell derived material cultured in both MS and SH media. The findings presented herein suggest that there is significant DNA removal at all DNase solution concentrations tested (0.25 mg/mL to 2 mg/mL). There were no statistically significant differences in DNA retention when treating the BY-2 cell-material cultured in SH media with all tested solution concentrations. With the material from BY-2 cells cultured in MS media however, the 1 mg/mL solution concentration produced DNA removal (<90%) comparable to that of the 2 mg/mL solution (FIG. 9), while lower DNase solution concentrations removed ~80 to 60% of DNA content. Both material lines (i.e., those derived from BY-2 cells cultured in SH or MS media) were treated with a 1 mg/mL solution of DNase. FIG. 9A depicts the DNA content observed in BY-2 cell derived matrix cultured in SH media in response to differing concentrations of DNase solution. There was no statistical difference in DNA content across DNase solution concentrations from 2-0.0025 mg/mL, as shown in FIG. 9B, of the BY-2 cell derived matrix cultured in MS media in response to differing concentrations of DNase solution.

Figure 10A:
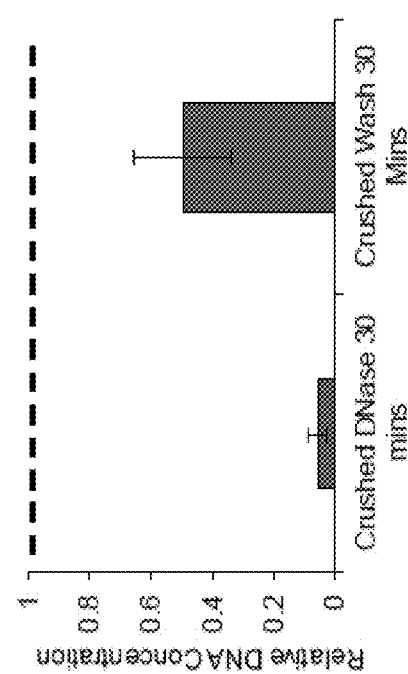
FIGS. 10A-10D depict results of rice cell processing.
Figure 10C:
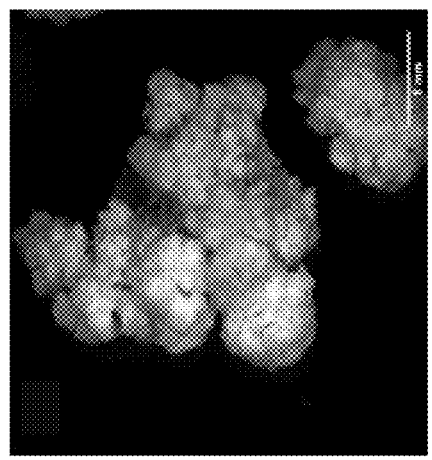
Figure 10B:
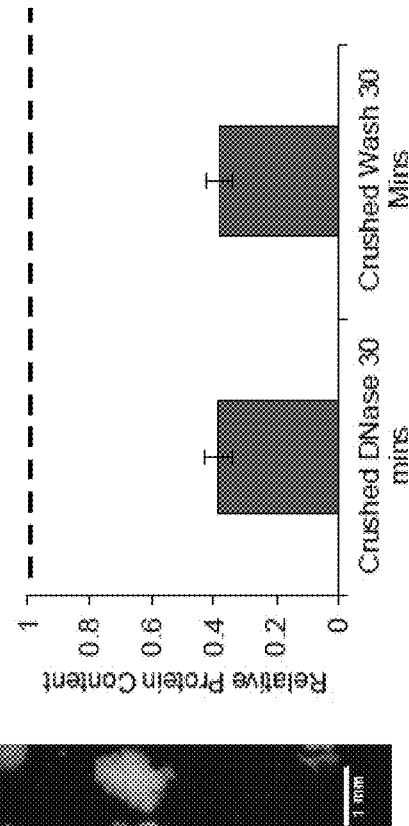
Figure 10D:
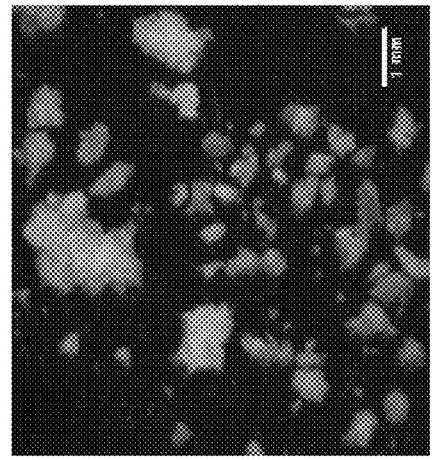
Figure 11:
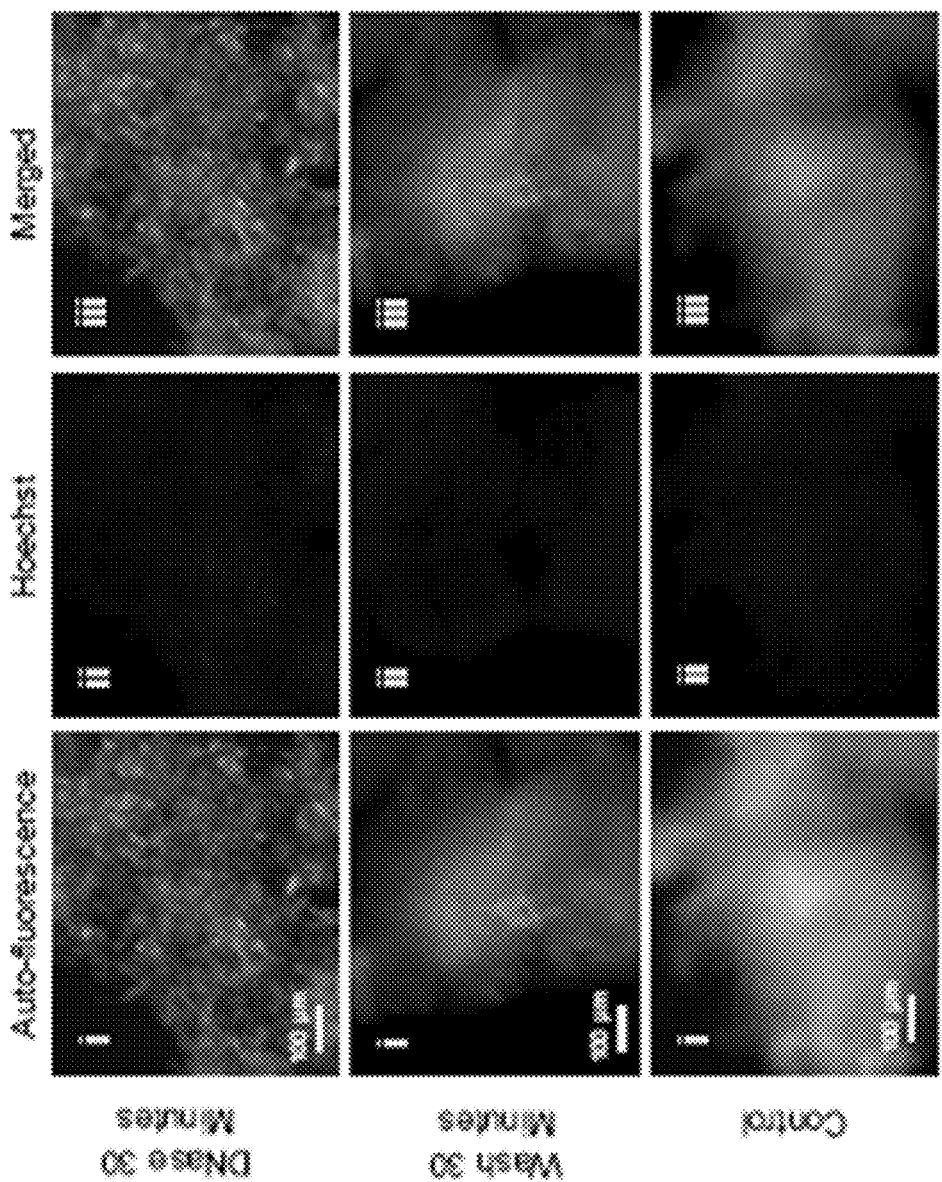
FIG. 11 depicts images of processed crushed rice cell.

Decellularization of rice cell-derived matrix. To evaluate the efficacy of the presently described decellularization treatment on other plant derived cell systems, similar techniques were applied to rice cell-derived cultures that expressed $(SP)_{32}$-EGFP. The rice matrices were crushed to provide better diffusion of the DNase throughout the material and thus be more effective at removing DNA material (FIGS. 10A and 10C). FIG. 10A depicts stereoscope image of untreated whole grain rice cell after lyophilization and FIG. 10C depicts stereoscope image of untreated crushed rice cells after lyophilization. A DNase treatment of 1 mg/mL for 30 mins was employed. The results show that 94% of the initial DNA is removed from the rice matrices using this decellularization method in comparison to the wash-treated and negative control groups (FIG. 10B). In particular, FIG. 10B shows relative DNA concentration of crushed rice cells after DNase or wash treatment for 30 mins. There is a greater than 90% reduction in DNA content in the DNase treated samples compared to the untreated control. Similar nuclei changes were observed in the rice cell-derived matrix as in the BY-2 cell-derived matrix (FIG. 11). FIG. 11 shows Hoescht staining that allowed for visualization of rice cell nuclei after processing with DNase, wash, or no treatment. There is a noticeable presence of intact nuclei throughout material in the wash-treated and control samples while the DNase treated materials exhibit a more diffuse staining due to autofluorescence. Additionally, ~60% reduction in protein retention occurred in both the 30-min wash and DNase treated samples compared the control group (FIG. 10D). In particular, FIG. 10D shows protein retention of crushed rice cells after DNase or wash treatment for 30 min. Similar losses of protein (~60%) in both treatment groups suggests that protein is lost through aqueous leaching within the first 30 mins of treatment. The DNA reduction and protein retention were similarly effective as observed for the BY-2 material, suggesting that this procedure for decellularization is effective in multiple plant culture models. These results demonstrate other viable applications of the decellularization technique disclosed herein in maintaining functional protein after treatment.

Figure 12A:
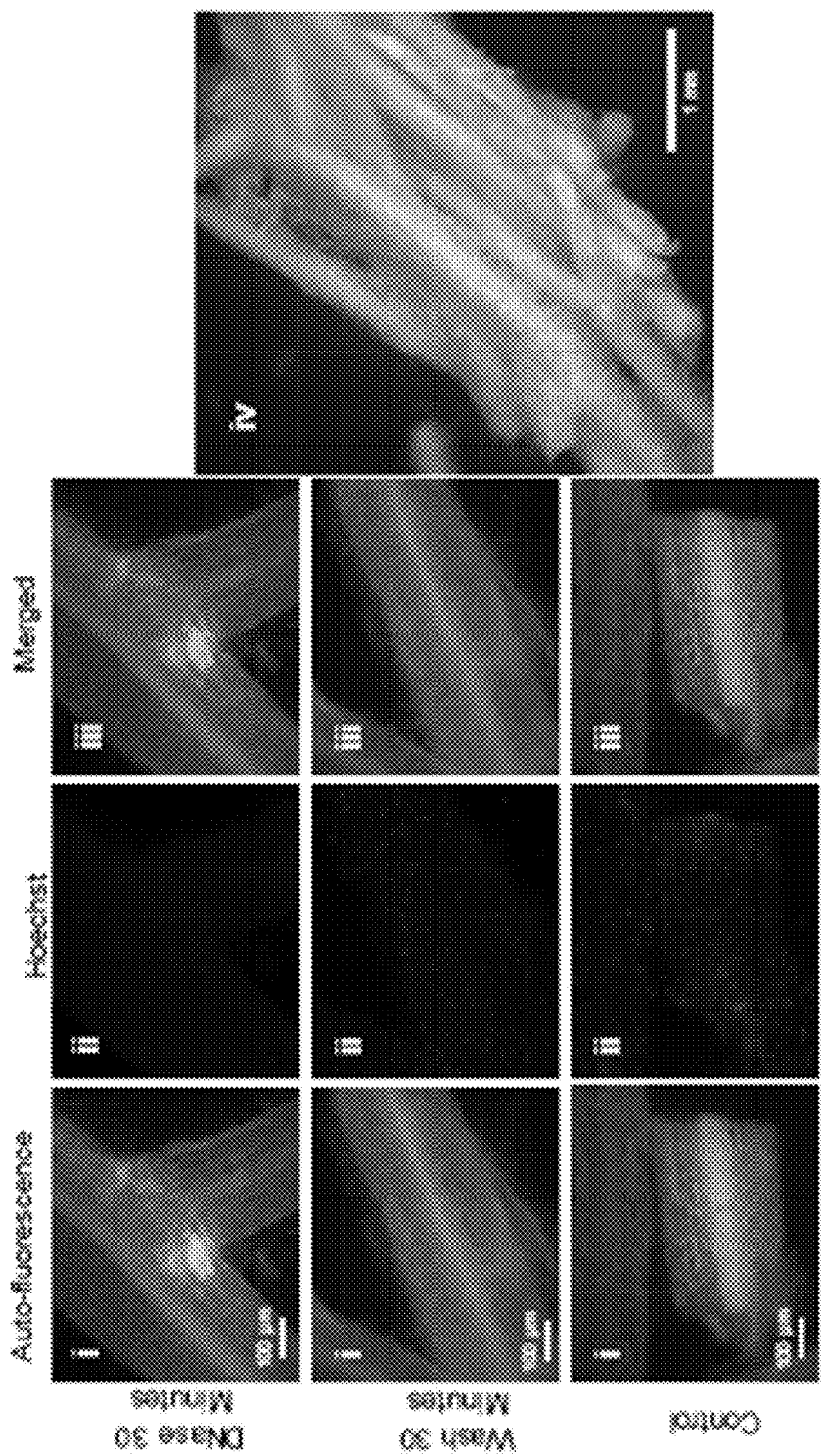
FIGS. 12A-12C depict results of hairy root processing.
Figures 12B, 12C:
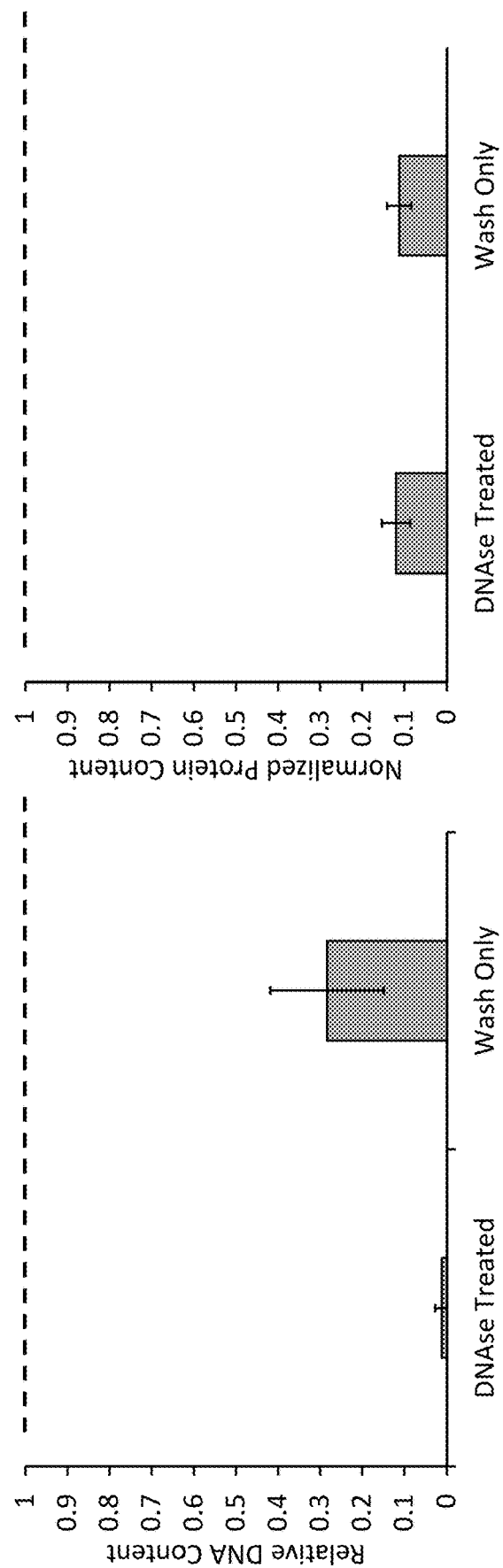

Decellularization of hairy root cell-derived matrix. The efficacy of the decellularization methods were determined when applied to 3D plant cultures. Hairy roots derived from transgenic tobacco were treated with 1 mg/mL DNase for 30 min, then preserved in 4% PFA for further analysis. A similar decline in DNA retention in response to DNase treatment was observed as demonstrated through nuclei staining (FIG. 12A) in comparison to the BY-2 plant cell derived matrices. FIG. 12A shows hairy root culture samples that were treated with the decellularization treatment previously applied to the BY-2 cells. A dramatic reduction in nuclei (Hoechst) after applying DNase treatment for 30 mins was observed as opposed to wash-treated and untreated samples.

Figure 13:
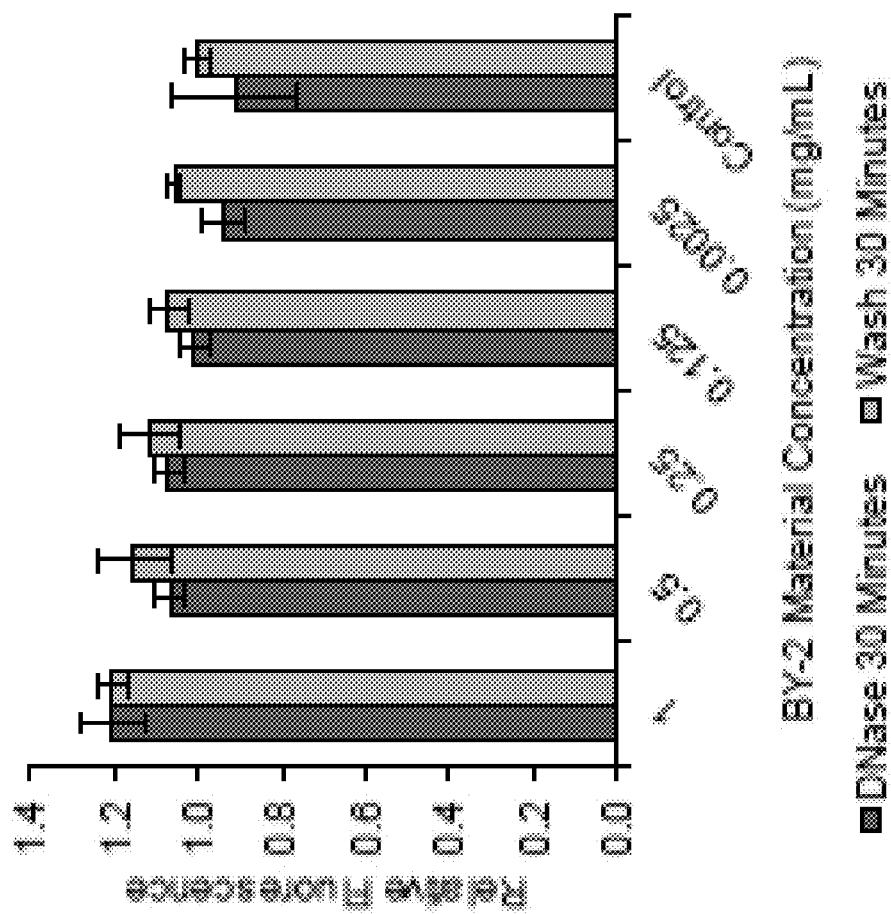
FIG. 13 is a graph that depicts human foreskin fibroblasts (hFF) monolayer cytotoxicity at different concentrations of BY-2 material.

BY-2 cell-derived matrix induced increased fibroblast viability. After confirming the decellularization efficacy of the treatment method, the biocompatibility of the material was evaluated. In particular, hFFs were initially exposed to BY-2 cell-derived matrix derived from BY-2 cells that had been treated with between 0.0025 mg/mL and 1 mg/mL DNase or were treated with wash only. The hFFs were exposed for three days to determine a suitable treatment concentration of matrix to perform a time course experiment (FIG. 13). FIG. 13 shows metabolic activity of hFF that was measured after three days of exposure to differing concentrations (1-0.0025 mg/mL) of matrix derived from BY-2 cells cultured in MS media. A concentration dependent increase in hFF viability was observed. Therefore, subsequent studies were performed with 1 mg/mL matrix. hFFs were exposed to BY-2 matrix derived from BY-2 cells treated with DNase or wash only for 1 d, 3 d, and 7 d. Media derived from DNase treated BY-2 derived matrix, whether cultured in SH or MS, elicited significantly higher hFF viability when compared to the wash-treated group (FIGS. 14A and 14B). In particular, FIG. 14A shows hFF cell viability normalized to Day 1 exposed to BY-2 matrix derived from BY-2 cells cultured in SH media. FIG. 14B shows hFF cell viability normalized to Day 1 exposed to BY-2 matrix derived from BY-2 cells cultured in MS media. FIG. 14C shows the hFF morphology after 7 days of exposure to BY-2 matrix. The data demonstrates that the BY-2 matrix provides additional surface area and structure for the cells to infiltrate and proliferate within, confirming the matrix's potential as a tissue engineering construct. Moreover, the lack of DNA material in the decellularized matrices provide a more biocompatible platform for cells compared to controls (i.e., wash-treated samples).

hFF response to culturing in 3D BY-2 cell derived-matrix aggregate model. Seeding hFFs with BY-2 cell derived-matrix particles allowed for cellular proliferation when cultured in a 3D platform, leading to aggregate formation. The EGFP tagged BY-2 material autofluoresced under the FITC channel, Hoechst staining allowed for hFF nuclei imaging, and the actin filaments in the hFFs were stained with phalloidin. Confocal imaging showed that the hFFs re-populated the surface of the plant material while also demonstrating cellular infiltration throughout the BY-2 matrices (FIG. 15A). In particular, FIG. 15A depicts images that show that the hFFs grew throughout the BY-2 cell material aggregate both in the gelatin coated and noncoated aggregates. Aggregates formed by BY-2 cell material treated with DNase solution doubled in cellularity on day 14 in comparison with day 7 (FIG. 15B), whereas the BY-2 cell material treated with DNase solution and then gelatin coated provided no change in cell proliferation from day 7 to day 14 (FIG. 15B). FIG. 15B shows DNA content of BY-2 cell derived matrix aggregates with seeded hFFs normalized to day 7. However, both conditions showed cell attachment and repopulation on the decellularized BY-2 derived matrix.

Figure 16:
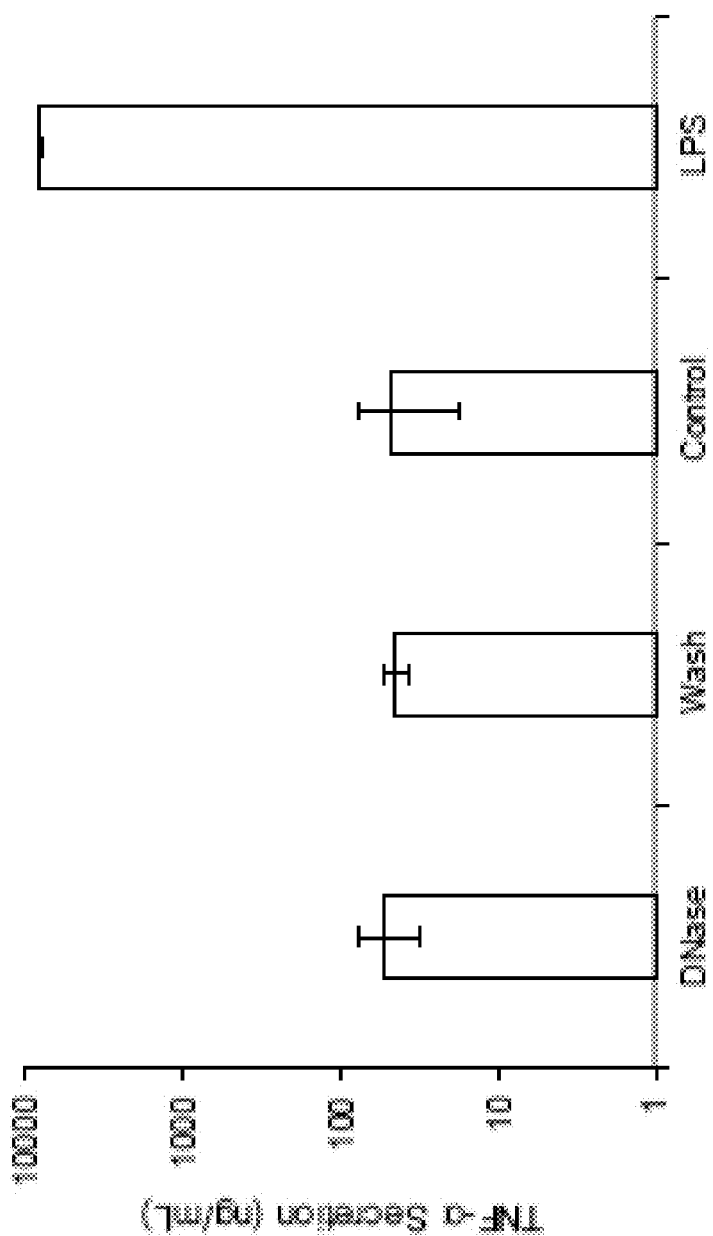
FIG. 16 depicts TNF-α release response to inflammation.

Macrophage Response. TNF-α release was measured 48 hours after M0 macrophage exposure to media containing potential leached material from the BY-2 cell derived material. The concentrations of TNF-α were not statistically significant between the control, wash treatment, and DNase treatment groups, demonstrating that decellularized BY-2 derived plant matrices do not incite a strong inflammatory response, which is already more than tenfold lower than that observed when M0s macrophages were exposed to lipopolysaccharide (LPS) (FIG. 16). In particular, FIG. 16 depicts TNF-α release that was measured via ELISA. TNF-α concentrations show no statistically significant differences between the DNase-treated, wash-treated, and control groups.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It can be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

We claim:

1. A method for decellularizing cells, the method comprising:
    contacting a plurality of plant cells with a composition comprising a nuclease comprising DNase, thereby decellularizing the plurality of plant cells, wherein the plurality of plant cells are cellulose producing plant cells.

2. The method of claim 1, wherein the DNase is DNaseI.

3. The method of claim 1 further comprising culturing the plurality of plant cells prior to contacting the cells with the nuclease.

4. The method of claim 3, further comprising isolating cellular material from the cultured plurality of plant cells.

5. A method of producing a biocompatible scaffold in vitro, the method comprising:
  contacting cellulose producing cultured plant cells with a composition comprising a DNase, thereby producing decellularized cultured plant cells; and
  creating a biocompatible scaffold in vitro from the decellularized [modified] cultured plant cells.

6. The method of claim 5 further comprising modifying the cellulose producing cultured plant cells to express a bioactive agent.

7. The method of claim 6, wherein the bioactive agent is a molecule that directs mammalian cell expansion, differentiation, or a cellular response.

8. The method of claim 6, wherein the bioactive agent is imbedded, attached, or associated with cell walls of the cellulose producing cultured plant cells.

9. The method of claim 5, wherein the DNase is DNaseI.

10. The method of claim 5, wherein the composition further comprises trypsin, collagenase, lipase, dispase, thermolysin, and α-galactosidase.

11. The method of claim 1 further comprising, prior to contacting, subjecting the plurality of cultured plant cells to lyophilization.

12. The method of claim 5 further comprising, prior to contacting, subjecting the cultured plant cells to lyophilization.

* * * * *